US00PP16623P3

(12) United States Plant Patent
Carruth

(10) Patent No.: US PP16,623 P3
(45) Date of Patent: Jun. 6, 2006

(54) SHRUB ROSE PLANT NAMED 'WEKFABPUR'

(50) Latin Name: *Rosa hybrida*
Varietal Denomination: WEKfabpur

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 45 days.

(21) Appl. No.: 10/966,541

(22) Filed: Oct. 15, 2004

(65) Prior Publication Data

US 2006/0085875 P1 Apr. 20, 2006

(51) Int. Cl.
*A01H 5/00* (2006.01)

(52) U.S. Cl. ..... Plt./102

(58) Field of Classification Search ..... Plt./102, Plt./141, 130
See application file for complete search history.

(56) References Cited

PUBLICATIONS

Weeks Roses. Midnight Blue (Trademark) 2005 Intro [online] [retrieved on May 4, 2005]. Retrieved from the Internet:: <http://www.weeksroses.com/midnightblue.php>.*

* cited by examiner

*Primary Examiner*—Anne Marie Grunberg
*Assistant Examiner*—June Hwu

(57) ABSTRACT

A new variety of Shrub rose suitable for garden decoration, having flowers of velvety black purple coloration with a white eye.

1 Drawing Sheet

Classification: The present invention relates to a new *Rosa hybrida* plant.

Variety denomination: The new plant has the varietal denomination 'WEKfabpur'.

BACKGROUND OF THE INVENTION

This invention relates to a new and distinct variety of Shrub Rose. It has an undisseminated seedling of my creation as its seed parent with the following genetic origin [(Sweet Chariot×Blue Nile)×Stephen's Big Purple] and an undisseminated seedling of my creation as pollen parent with the following genetic origin [(International Herald Tribune×*Rosa soulieanna* derivative)×(Sweet Chariot×Blue Nile)].

SUMMARY OF THE INVENTION

Among the features which distinguish the new variety from other presently available and commercial rose cultivars known to the inventor are the following combination of characteristics: its thornless new shoots, branches and rachis, its flowers of velvety black purple coloration and its strong clove to spicy fragrance. The plant has a bushy compact growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKfabpur' may be asexually propagated by budding and grafting. The budding and grafting successfully plant/rootstock *Rosa hybrida* cv. Dr. Huey.

COMPARISON WITH PARENTS

The new rose may be distinguished from its seed parent, an undisseminated seedling of my creation by the following combination of characteristics: whereas 'WEKfabpur' bears medium sized flowers (about 5.3 to about 7.4 cm. in diameter) of velvety black purple coloration and with semi-double petalage (about 18 to 24 petals), the undisseminated seedling bears significantly larger flowers (about 7.3 to 8.9 cm in diameter) of purple-pink coloration with more double petalage (about 29 to 35 petals). The seed parent bears foliage with a very glossy finish, whereas 'WEKfabpur' bears foliage with a semi-glossy finish.

The new variety may be distinguished from its pollen parent, an undisseminated seedling of my creation by the following combination of characteristics: whereas the undisseminated seedling bears moderately small flowers (about 3.3 to 4.2 cm. in diameter) and with semi-double petalage (about 7 to 9 petals), 'WEKfabpur' bears significantly larger flowers (about 5.3 to about 7.4 cm. in diameter) with more double petalage (about 18 to 24 petals). The pollen parent is a floribunda rose with a medium-tall spreading mature habit, whereas 'WEKfabpur' is classified as a shrub rose with a significantly shorter and more compact mature growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety usually bears its flowers in clusters of four to five per stem. Flowers are borne in somewhat regular rounded clusters on strong short to medium stems (about 26 to about 72 cm.). Outdoors, the plant blooms abundantly and nearly continuously during the growing season. The flowers have a strong clove to spicy fragrance.

BUD

The peduncle is about 2.4 to about 5.2 cm. in length, of average caliper (about 0.15 to about 0.25 cm. in diameter), and usually erect. It is almost entirely smooth, with some stipitate glands and hairs. Peduncle color is between 144A and 135C.

Before the calyx breaks, the bud is about 0.8 to about 1.2 cm. in diameter at the widest point, about 1.0 to about 1.5 cm. in length, and very pointed in shape. The surface of the bud bears few foliaceous appendages and many hairs, usually with slender entire foliaceous parts extending beyond the tip of the bud about ½ or more of its length. Bud color is between 144A and 135C.

The sepals are about 2.2 to about 3.0 cm. in length and about 0.6 to about 1.0 cm. in width at the widest point. The outer surface color of the sepal is between 144A and 135C. The inner surface color of the sepal is between 138B and 137C and covered with fine wooly tomentum; sepal margins are lined with some stipitate glands and hairs.

The receptacle is of somewhat short length (about 0.5 to about 0.8 cm.) and of average caliper (about 0.6 to about 0.8 cm. in diameter). The receptacle is globular to almost rounded in form. It surface is very smooth with thick fleshy walls. The receptacle color is between 144A and 135C.

As the petals open (after the calyx breaks), the bud is about 1.2 to about 2.0 cm. in diameter at the widest point, about 1.8 to about 2.4 cm. in length, and moderately pointed to somewhat ovoid in form. The color of the under surfaces of the newly opened petals is between 60A and 59B at the center of the petal suffusing to as dark as between 187A and 187B toward the edge of the petal. At the point where the petal attaches, there is moderately large zone of between 3D and 5D. The color of the upper surfaces of the newly opened petals is between 60A and 60B at the center of the petal suffusing to darker than between 79A and 187A toward the edge of the petal. At the point where the petal attaches, there is a moderately large zone of between 8B and 10A. Sometimes on either side of this attachment point, extending to the edge of the petal, there is a somewhat wide, diagonal zone of lighter coloration forming a broad 'V'. The coloration of this chevron is between 2D and 4D.

BLOOM

When fully open, the bloom ranges from about 5.3 to about 7.4 cm. in diameter. Petalage is semi-double with 18 to 24 petals and about 2 to 8 petaloids irregularly arranged. Petaloids are about 0.8 to about 1.2 cm. in length and about 0.3 to about 0.6 cm. in width at the widest point. Petaloids are shaped moderately oblanceolate to somewhat oblong with rounded apices. When partially open, the bloom form is cupped to somewhat globular, and the petals are loosely cupped with petal edges somewhat reflexed outward. When fully open, the bloom form is less cupped to somewhat flat, and the petals are loosely cupped with petal edges somewhat reflexed outward.

PETALS

The substance of the petals is somewhat light and of moderately thin thickness, with upper surfaces moderately velvety to somewhat satiny and under surfaces slightly shiny to matte. The outer petals are nearly round in shape with apices usually somewhat mucronate. The inner petals are moderately obovate to somewhat oblanceolate in shape with apices usually somewhat mucronate to sometimes rounded. The petals are about 2.1 to about 3.0 cm. in length and about 1.3 to about 2.7 cm. in width at the widest point. Petal margins are entire.

NEWLY OPENED FLOWER

The under surface color of the outer, intermediate and inner petals is between 60B and 72B at the center of the petal suffusing to as dark as between 79B and 187B toward the edge of the petal and rarely showing irregular striped and flecked of near 155D in coloration. At the point where the petal attaches, there is a moderately large zone of near 4D. The upper surface color of the outer, intermediate and inner petals is between 60A and 72A near the center of the petal that gradually suffuses to darker than between 79A and 187A toward the edge of the petal. At the point where the petal attaches, there is a moderately large zone of between 4C and 2D. Sometimes on either side of this attachment point, extending to the edge of the petal, there is a moderately wide, nearly horizontal zone of lighter coloration forming a broad 'V'. The coloration of this chevron is near 4D. The under and upper surface color of the petaloids are similar in coloration to the upper and under surfaces of the intermediate petals.

The general tonality of the newly opened flower is between 60A and 72A near the center of the petal that gradually suffuses to darker than between 79A and 187A toward the edge of the petal. Sometimes at the very center of the flower, there is a 'eyezone' pattern consisting of the basal attachment zone of between 4C and 2D and the chevron marking of near 4D in coloration.

THREE-DAY-OLD FLOWER

The under surface color of the outer, intermediate and inner petals is between 72B and 79D at the center of the petal suffusing to as dark as between 77A and 187C toward the edge of the petal and rarely showing irregular striped and flecked of near 155D in coloration. At the point where the petal attaches, there is a moderately large zone of between 4D and 155C. The upper surface color of the outer, intermediate and inner petals is between 72A and 187C near the center of the petal that gradually suffuses to as dark as between 79B and 187B toward the edge of the petal. At the point where the petal attaches, there is a moderately large zone of near 4D. Sometimes on either side of this attachment point, extending to the edge of the petal, there is a moderately wide, nearly horizontal zone of lighter coloration forming a broad 'V'. The coloration of this chevron is near 155C. The under and upper surface color of the petaloids are similar in coloration to the upper and under surfaces of the intermediate petals.

The general tonality of the three-day-old flower is between 72A and 187C near the center of the petal that gradually suffuses to darker than between 79B and 187B toward the edge of the petal. Sometimes at the very center of the flower, there is a 'eyezone' pattern consisting of the basal attachment zone of near 4D and the chevron marking of near 155C in coloration.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 95) and are arranged regularly about the pistils; a few are mixed with petaloids. The filaments are of somewhat short length (about 0.2 to about 0.7 cm.), most with anthers. Filaments are near 13B in color usually moderately suffused with near 53B. The anthers are moderately small for the class and all open approximately at the same time. Anther color is between 18A and 20A when immature and between 163A and 200A at maturity. Pollen is abundant and between 20A and 22B in color.

FEMALE REPRODUCTIVE ORGANS

Pistils vary in number (average about 35). The styles are moderately even, average in length (about 0.5 to about 0.8 cm.), average in caliper, and loosely bunched. Stigma color is between 20C and 19B. Style color is between 2D and 4D often heavily suffused with between 187C and 183B. Ovaries are usually all enclosed in the calyx.

Hips have not been observed on this variety when grown in Upland, Calif.

FOLIAGE

The compound leaves are usually comprised of three to seven leaflets and are borne abundantly. The seven-leaflet leaves are about 11.5 to about 15.2 cm. in length and about 8.2 to about 9.6 cm. in width at the widest point, somewhat thin to moderately leathery in texture, and semi-glossy in finish. The terminal leaflets are about 5.3 to about 6.2 cm. in length and about 2.6 to about 3.5 cm. in width at the widest point, shaped moderately ovate to somewhat oval with acute apices and rounded bases. Their margins are usually simply serrate.

The upper surface color of the mature leaf is between 147A and 131B. The under surface color of the mature leaf is between 137B and 135C. The upper surface color of the young leaf is between 147A and 141C, sometimes moderately suffused with between 187A and 183A. The under surface color of the young leaf is between 146B and 135C, sometimes lightly suffused with between 187A and 183A.

The rachis is moderately light in caliper and very smooth. The upper side is shallowly grooved with some hairs and few stipitate glands on the edges of the grooves. The under side of the rachis is very smooth with few hairs. The rachis color is between 144A and 135C sometimes moderately suffused, especially on the young leaves with between 187C and 183C.

The stipules are about 1.1 to about 1.5 cm. in length and of moderately narrow width (about 0.4 to about 0.6 cm.) with somewhat long straight points that usually turn out at an angle of more than 45 degrees and sometimes recurve toward the stem. The stipules color is between 144A and 135C sometimes moderately suffused, especially on the young leaves with between 187C and 183C.

The petiole is moderately light in caliper and very smooth. It is about 0.6 to about 1.4 cm. in length and about 0.1 to about 0.2 cm in diameter at the widest point. The upper side is shallowly grooved with some hairs and few stipitate glands on the edges of the grooves. The under side of the petiole is very smooth with few hairs. The petiole color is between 144A and 135C sometimes moderately suffused, especially on the young leaves with between 187C and 183C.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a bushy compact low to medium height growing habit (about 75 to about 92 cm. in height and about 46 to about 60 cm. spread at the widest point), with full branching. It displays moderately vigorous growth and the canes are of somewhat light to medium caliper for the class.

The color of the major stems is between 146A and 146B. They bear none to very few medium size prickles that are about 0.4 to about 0.6 cm. in length. The medium size prickles are almost straight and angled slightly downward with a somewhat short length narrow oval base; prickle color is between 164A and 165B. The major stem bears no small prickles.

The color of the branches is between 144A and 135C. They bear no large or small prickles.

The color of the new shoots is between 144A and 135C sometimes lightly suffused with between 187A and 183A. They bear no large or small prickles.

I claim:

1. A new and distinct Shrub rose plant of the variety substantially as described and illustrated herein.

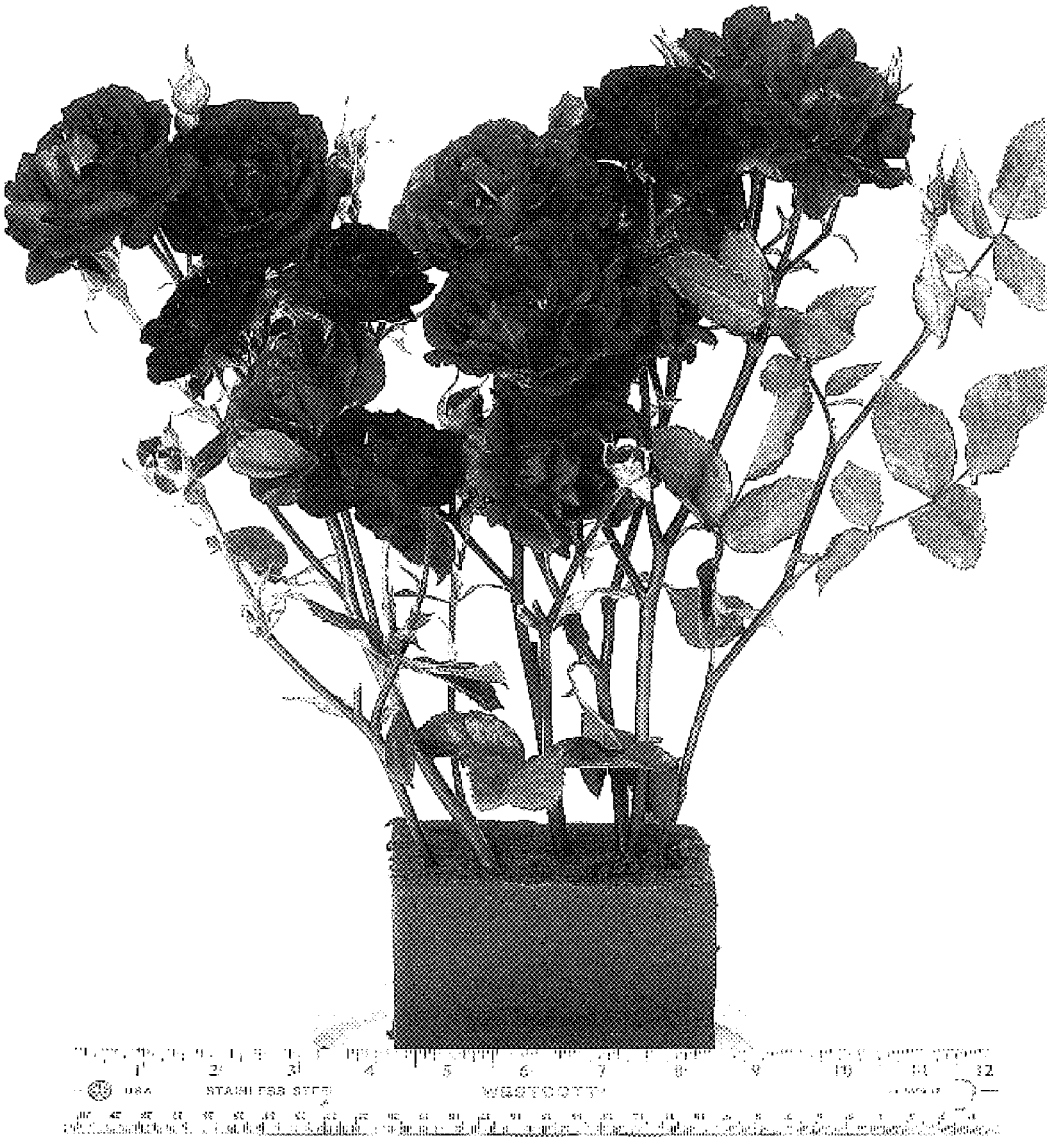

* * * * *